(12) United States Patent
Franck et al.

(10) Patent No.: US 7,926,326 B2
(45) Date of Patent: Apr. 19, 2011

(54) SYSTEM AND METHOD FOR INTERFACIAL RHEOMETRY

(75) Inventors: Aloyse Franck, Kleinostheim (DE); Jan Vermant, Meise (BE); Gerald G. Fuller, Stanford, CA (US)

(73) Assignee: Waters Technologies Corporation, New Castle, DE (US)

( * ) Notice: Subject to any disclaimer, the term of this patent is extended or adjusted under 35 U.S.C. 154(b) by 414 days.

(21) Appl. No.: 12/204,545

(22) Filed: Sep. 4, 2008

(65) Prior Publication Data
US 2009/0056423 A1   Mar. 5, 2009

Related U.S. Application Data

(60) Provisional application No. 60/970,115, filed on Sep. 5, 2007.

(51) Int. Cl.
*G01N 11/14* (2006.01)
*G01N 11/16* (2006.01)

(52) U.S. Cl. .......... 73/54.39; 73/54.23; 73/54.31; 73/54.37

(58) Field of Classification Search .......... 73/53.01, 73/53.05, 54.01, 54.23, 54.25, 54.27, 54.28, 73/54.31, 54.32, 54.37, 54.39
See application file for complete search history.

(56) References Cited

U.S. PATENT DOCUMENTS

| 1,817,739 A * | 8/1931 | Dintilhac | 73/54.28 |
|---|---|---|---|
| 2,796,758 A * | 6/1957 | Myers et al. | 73/54.32 |
| 3,496,762 A * | 2/1970 | Gaeta | 73/54.01 |
| 3,803,903 A * | 4/1974 | Lin | 73/54.31 |
| 2003/0233867 A1 * | 12/2003 | Hall | 73/54.28 |
| 2008/0034844 A1 * | 2/2008 | Manneville | 73/54.23 |

FOREIGN PATENT DOCUMENTS

| JP | 56122933 A | * | 9/1981 |
|---|---|---|---|
| JP | 56150328 A | * | 11/1981 |

OTHER PUBLICATIONS

"A Trough With Radial Compression For Studies Of Monolayers and Fabrication Of Langmuir-Blodgett Films", M. Matsumoto, Y. Tsujii, K-I. Nakamura and Y. Yoshimoto, Thin Solid Films 280 1,2 (1996) 238-243.

* cited by examiner

*Primary Examiner* — David A. Rogers
(74) *Attorney, Agent, or Firm* — Paul, Hastings, Janofsky & Walker LLP; Aslan Baghdadi

(57) ABSTRACT

An apparatus and method for performing rheological measurements of interfaces located at the top of fluid sub-phases. In one configuration, a rotating rheometer is provided with a chamber wall whose inner surface defines an outer chamber radius and an inner cylinder disposed within the cylindrical chamber and having an inner chamber radius. The rotating rheometer is configured to hold a liquid sub-phase and interface layer that can be probed using a circular ribbon that is concentric with and suspended between the inner cylinder and chamber wall. The ratio of the ribbon radius, inner chamber radius, and outer chamber radius is designed to yield an average shear rate in the inner region that is the same as an average shear rate in the outer region. In one configuration, an interface-pinning feature is provided on at least one of the inner cylinder and the chamber wall.

27 Claims, 11 Drawing Sheets

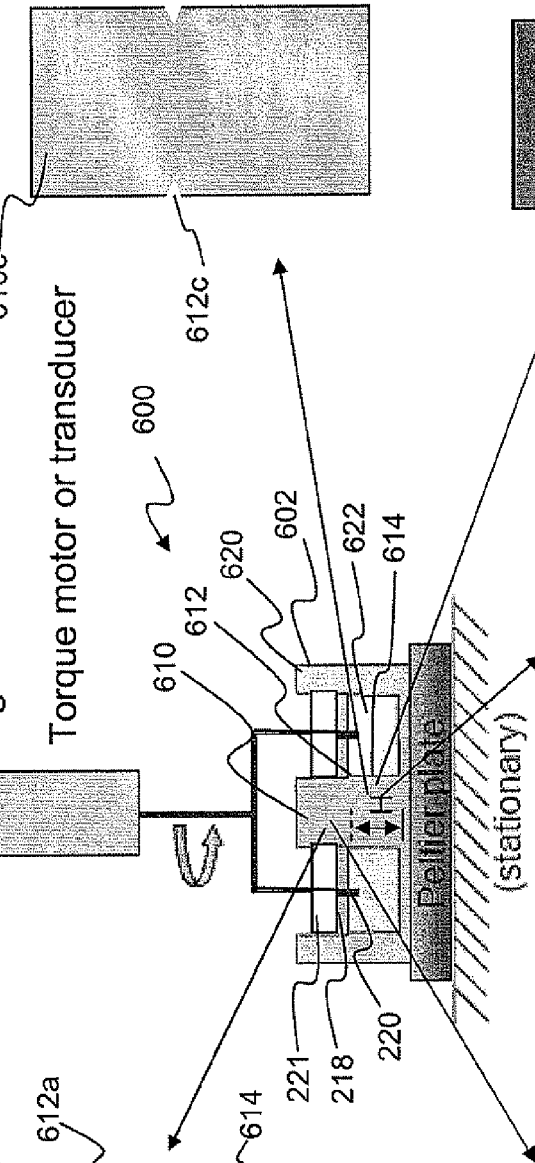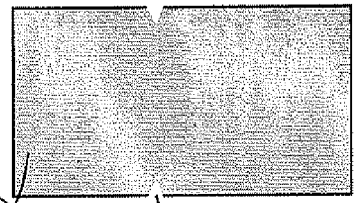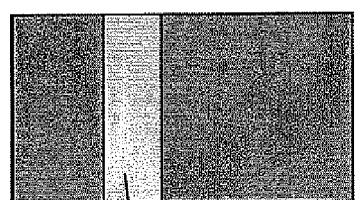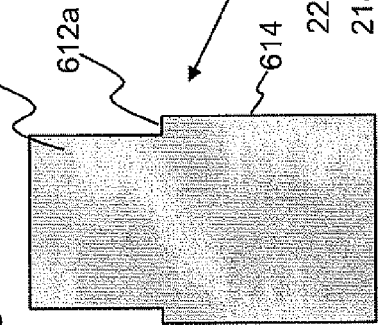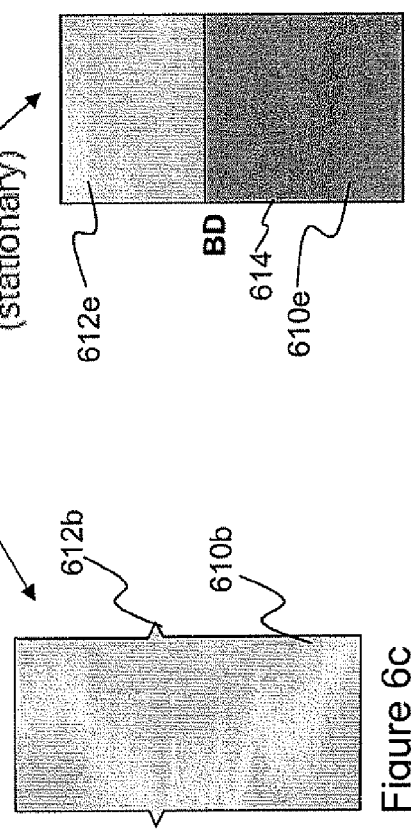

SYSTEM AND METHOD FOR INTERFACIAL RHEOMETRY

The present invention claims priority to U.S. Provisional Patent Application No. 60/970,115, filed Sep. 5, 2007 and incorporated by reference herein in its entirety.

BACKGROUND

Field of the Invention

The present invention relates generally to rheology and more specifically to systems for measuring rheological properties of thin layers and interfaces disposed on sub-phases.

Measurement of the mechanical properties of interfaces and surfaces can be performed using instruments such as rheometers by specially adapting such instruments to probe the surfaces. These properties are especially of interest in characterizing food materials and cosmetics whose mechanical properties are highly dependent on the interaction at the interface between two or more phases. Typically, in known systems for measuring interfaces, a ring or a bicone is introduced into an interface layer; for example, a monolayer disposed on a fluid sub-phase contained in a cylindrical chamber. The ring can be rotated or the chamber can be rotated to obtain information concerning the mechanical properties of the surface layer. The measurement of mechanical properties of an interface layer disposed on a sub-layer can provide insight into the mechanical properties of systems in which the interface material is dispersed with a large interfacial region within the sub-layer. For example, surfactants in a liquid phase, sols and gels all comprise multiphase systems in which one phase is microscopically dispersed within a second phase. Instead of dispersing a first phase within another phase (host phase), the first phase can be disposed as a thin layer on the host phase (sub-phase), such as a monolayer on a liquid. The monolayer can then be measured in contact with the sub-phase using known rheometers to gain insight into the behavior of the monolayer phase when dispersed within the sub-phase. Accordingly, it is desirable to provide accurate measurements of the mechanical properties of surface (interface) layers.

Calculations of shear properties of the interface layer in such known rheometer systems often assume that the interface region that lies inside the ring is rotating in unison with the ring. However, in the region of the sub-phase below the interface region inside the ring, energy may be introduced into the interface layer that affects the rotation of the interface layer inside the ring. Because of this, known measurement approaches that fail to account for effects from a sub-phase located within the ring are subject to significant inaccuracies.

Accordingly, there is a need to improve rheometric measurements for interface layers disposed on subphases.

BRIEF SUMMARY OF THE INVENTION

In one configuration of the present invention, a system for measuring the rheological properties of a fluid interface comprises a cylindrical chamber having a chamber wall whose inner surface defines an outer chamber radius with respect to an axis of the cylindrical chamber, wherein the chamber wall is configured to retain a fluid therein. The system includes an inner cylinder disposed within the cylindrical chamber and concentric with an axis of the cylindrical chamber, wherein the inner cylinder has an outer surface defining an inner cylinder radius, wherein the inner cylinder is mechanically coupled to the chamber wall to prevent relative rotational or translational movement between the inner cylinder and chamber wall.

The system further includes a circular ribbon that can have various cross section shapes, such as rectangular or diamond shapes. The circular ribbon is concentric with and suspended between the inner cylinder and chamber wall and configured to contact the interface. The circular ribbon has a ribbon radius that is intermediate between the inner cylinder and outer chamber radii. In one embodiment of the invention, the ribbon comprises a diamond structure in cross-section that promotes coupling of the ribbon surface by the interface phase region in contact with the ribbon. The system is configured to impart a relative rotation to the circular ribbon with respect to the chamber wall and inner cylinder. Preferably, the ribbon is coupled through a suspension system to a torque motor or torque transducer. In one embodiment, the ribbon is suspended from the torque transducer to contact the fluid interface in the cylindrical chamber, while a rotation is applied to the chamber, such that the chamber wall and inner cylinder rotate with a common angular velocity or acceleration with respect to the ribbon. In another embodiment, the chamber is held stationary while the ribbon is rotated using a torque motor from which the ribbon is suspended while contacting the fluid interface.

When the circular ribbon contacts the fluid interface, the circular ribbon defines an inner region that lies between the circular ribbon and inner cylinder and an outer region that lies between the circular ribbon and chamber wall. In accordance with an embodiment of the present invention, the values for the ribbon radius, inner chamber radius, and outer chamber radius are designed to yield an average shear rate in the inner region that is the same as an average shear rate in the outer region.

In accordance with another embodiment of the present invention, a method of measuring mechanical properties of an interface comprises filling a cylindrical measurement chamber with a liquid sub-phase until a meniscus of the liquid sub-phase is observed to disappear as a top surface of the sub-phase approaches a first height. The cylindrical measurement chamber has an inner cylinder defined by a radius $R_i$ that is concentric with an axis of the measurement chamber and an outer chamber wall defined by a radius $R_o$ and concentric with the measurement chamber axis and mechanically rigidly coupled to the inner cylinder. A further step includes lowering a circular ribbon onto the top surface of the sub-phase, wherein the circular ribbon has a radius $R_c$ that is intermediate between $R_i$ and $R_o$. An interface layer is introduced onto the top surface of the sub-phase and a relative rotational motion is induced between the circular ribbon and the cylindrical measurement chamber when the circular ribbon is in contact with the interface layer and the sub-phase.

In another embodiment of the present invention, a measurement system for measuring rheological properties of a fluid interface, comprises a substantially cylindrical chamber having an outer chamber wall whose inner surface defines an outer chamber radius with respect to an axis of the cylindrical chamber. The measurement system further comprises an inner cylinder disposed within the substantially cylindrical chamber and concentric with an axis of the substantially cylindrical chamber, the inner cylinder having an outer surface defining an inner chamber radius, wherein the inner cylinder is mechanically coupled to the outer chamber wall to prevent relative rotational or translational movement between the inner cylinder and chamber wall. The measurement system further comprises a circular ribbon concentric with and suspended between the inner cylinder and outer chamber wall and configured to contact the fluid interface, wherein the circular ribbon has a ribbon radius ($R_c$) that is intermediate between the inner cylinder ($R_i$) and outer chamber ($R_o$) radii. The measurement system additionally comprises a torque motor coupled to the circular ribbon through a suspension that is configured to impart to the circular ribbon a rotation that is concentric with the cylindrical chamber axis, a movable plate means that defines walls of an external chamber surrounding the cylindrical chamber, an aperture means to allow fluid to flow into the cylindrical chamber from the external chamber, and a drive motor configured to impart a relative translational motion to the walls of the movable plate means. The circular ribbon defines an inner region that lies between the circular ribbon and inner cylinder and an outer region that lies between the circular ribbon and outer chamber wall, wherein a ratio of the ribbon radius, inner chamber radius, and outer chamber radius is designed to yield an average shear rate in the inner region that is the same as an average shear rate in the outer region.

In accordance with an embodiment of the present invention, the circular ribbon is provided with an opening that interrupts the ribbon and facilitates communication between a liquid surface region disposed on the outside of the circular ribbon and contacting the outer surface of the circular ribbon, and a liquid surface disposed on the inside of the circular ribbon and contacting an inner surface of the circular ribbon. The measurement system is thereby configured to produce shear property measurements using the rotating ribbon as a function of compression of an interface fluid in the horizontal plane of the measurement system.

In another embodiment of the present invention, a measurement system for measuring rheological properties of a fluid interface, comprises a cylindrical chamber having a chamber wall whose inner surface defines an outer chamber radius with respect to an axis of the cylindrical chamber, the cylindrical chamber configured to retain a sub-phase that supports the fluid interface and an inner cylinder disposed within the cylindrical chamber and concentric with an axis of the cylindrical chamber, the inner cylinder having an outer surface defining an inner cylinder radius, wherein the inner cylinder is mechanically coupled to the chamber wall to prevent relative rotational or translational movement between the inner cylinder and chamber wall. The measurement system further comprises an interface-pinning feature that is preferably located on the inner cylinder as well as the outer cylinder. In accordance with an embodiment of the present invention, the interface-pinning feature defines a first boundary between a lower and upper cylindrical portion of the inner cylinder and a second boundary between a lower and upper cylindrical portion of the chamber wall, which first and second boundaries are located at the same height. The interface-pinning feature serves to pin an interface of a liquid whose surface is at the level of the interface-pinning feature, wherein a meniscus formation on the liquid is decreased or eliminated.

The measurement system also comprises a circular ribbon concentric with and suspended between the inner cylinder and chamber wall and configured to contact the interface, wherein the circular ribbon has a ribbon radius ($R_c$) that is intermediate between the inner cylinder ($R_i$) and outer ($R_o$) chamber radii, wherein the system is configured to impart a relative rotation to the circular ribbon with respect to the chamber wall and inner cylinder.

BRIEF DESCRIPTION OF THE DRAWINGS

FIGS. 6a-6f illustrate in a side cross-sectional view exemplary features of rheometric devices having an interface-pinning feature in the chamber walls, in accordance with alternative embodiments of the present invention.

DETAILED DESCRIPTION OF EMBODIMENTS OF THE INVENTION

Figure 1:
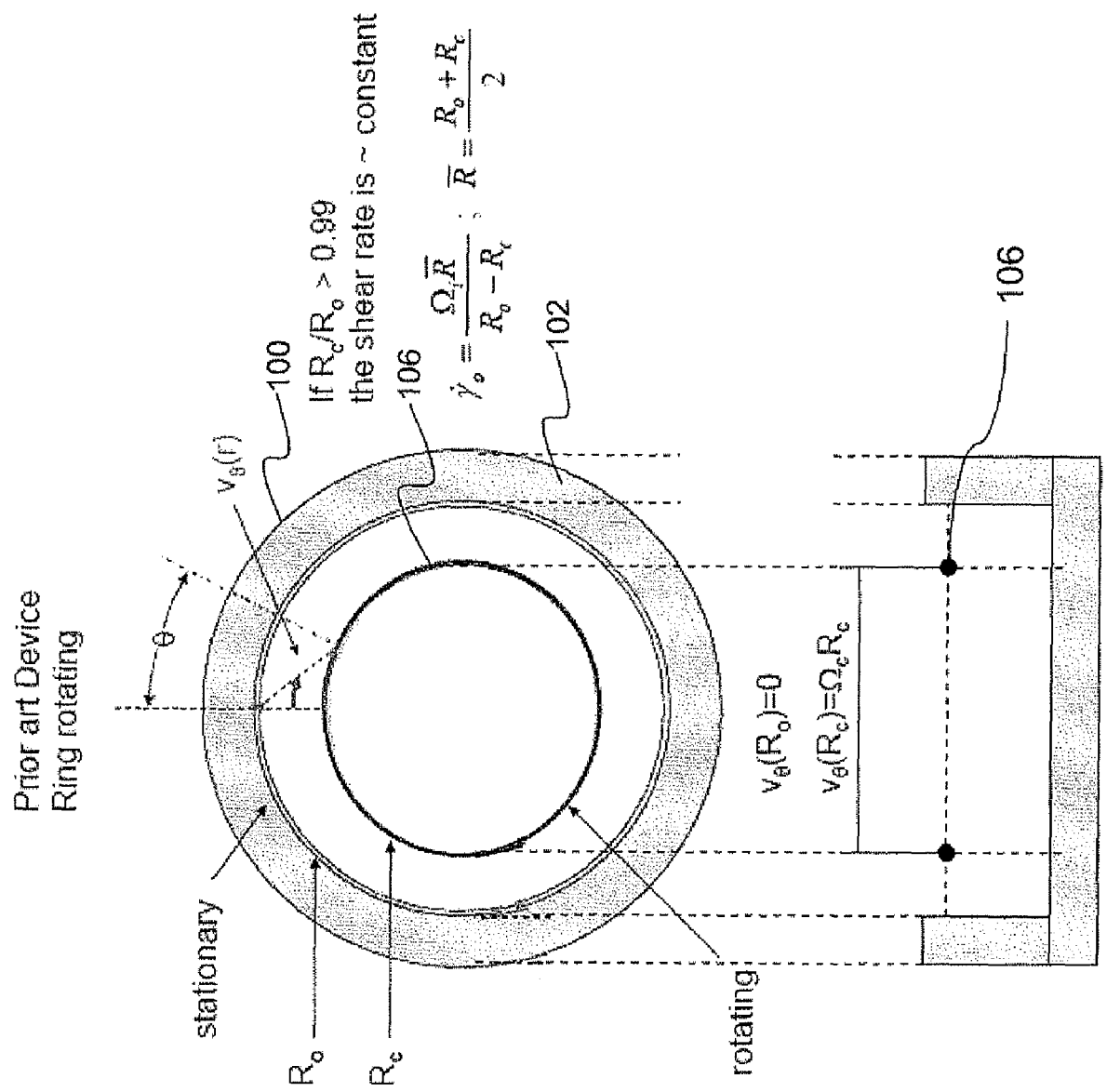
FIG. 1 illustrates a plan view together with side cross-sectional view of a rheometric device in accordance with the prior art.

In order to clarify the present invention, a known system is depicted in FIG. 1, and embodiments of the present invention are described below with respect to FIGS. 2a-8b.

Embodiments of the present invention are related to rheometric devices that facilitate measurement of fluid interfaces. The term "fluid interface," as used herein, generally refers to a surface region that is adjacent and contiguous to the body of a fluid. A fluid interface can be, for example, a monolayer of a material that is different from the fluid that is disposed under one surface of the fluid. Rheometric apparatus described herein operate to measure fluid interfaces at the top surface of a fluid contained within a rheometer chamber, which preferably is a cylindrical chamber. The "fluid interface" can alternatively comprise a region that is more than one monolayer thick. Unless otherwise indicated, the term "interface layer" is used herein synonymously with the term "fluid interface" to denote a thin layer that is disposed typically on a top surface of a fluid and having mechanical properties that in general are different from those of the bulk fluid. Notably, however, the "fluid interface" may only constitute a small portion of a second layer disposed on a fluid sub-phase. For example, the "fluid interface" or "interface layer" can constitute one or a few monolayers of a millimeter thick layer placed on top of a water sub-phase. The "interface layer" could also constitute a region of a few monolayers or less at the boundary between a liquid subphase and a gas, such as a monolayer region disposed at the interface between an aqueous sub-phase and air.

By providing a convenient and accurate method of measuring properties of a material disposed as an interface layer disposed on a fluid surface, the properties of systems that contain the fluid material and interface layer material in different configurations can be better understood. For example, the rheometric properties of a thin layer comprising an organic material disposed on a water sub-phase can be accurately probed in accordance with embodiments of the invention disclosed below. This can lend understanding to the behavior of the same organic material when the organic material is disposed in the bulk fluid (water) as an emulsion, for example.

In order to probe mechanical properties of fluid interfaces, rheometric devices have been developed that allow a ring or similar circular structure to contact the interface region while a shear is introduced into the fluid/interface system. FIG. 1 illustrates a top down view of a rheometric device 100 arranged with a ring structure for measuring fluid interfaces, in accordance with the prior art. Rheometer 100 is configured as a cylindrical chamber whose wall 102 has a first height that is configured to retain a fluid within the cylinder. The rheological properties of a surface layer disposed on a fluid in rheometer 100 can be measured by rotating ring 106 in unison while chamber wall 102 is held motionless.

In order to accurately measure the rheological properties of an interface layer, the shear rate should be well characterized. For example, the shear rate distribution of the chamber fluid can be calculated from knowledge of the angular velocity (or acceleration) of the rotating ring 106 and the distance between the ring 106 and chamber wall 102. By measuring the torque sustained by ring 106 in contact with an interface layer, and calculating the shear rate between ring 106 and wall 102, the mechanical properties of the interface layer can be calculated. As shown, the velocity $V_\theta$ is 0 at position $R_o$ corresponding to the radius of the inside wall of the chamber, while at radial position $R_C$ corresponding to the ribbon position, $V_\theta$ is $\Omega_C R_C$, where $\Omega_C$ is the angular velocity of the ribbon at position $R_o$. As shown, the shear rate $\gamma_o = \Omega R (R_o - R_c)$, where $\gamma_o$ is the shear rate, $\Omega$ is the angular velocity of the chamber wall, R is the average radius defined as $(R_o + R_c)/2$. If $R_c/R_o > 0.99$ and $R_i/R_c > 0.99$, the shear rate can be assumed to be constant, whereas if $R_c/R_o < 0.99$ and $R_i/R_c < 0.99$, curvature needs to be taken into account and the shear rate is a complex function of radius R. It is assumed that the interfacial layer inside of the ring 106 rotating with the ring is not subjected to a shear deformation and therefore does not contribute to the torque measurement.

However, since the sub-phase is stationary and the interfacial layer rotating, an ill defined shear rate is applied to the interface within the inner region of the ring 106 generating an unknown torque contribution. These shear rate contributions caused by the sub-phase in the inner region of the ring are not accounted for and cause the shear rate to be undefined in rheometric systems in which the chamber is configured as in FIG. 1.

Figures 2A, 2B:
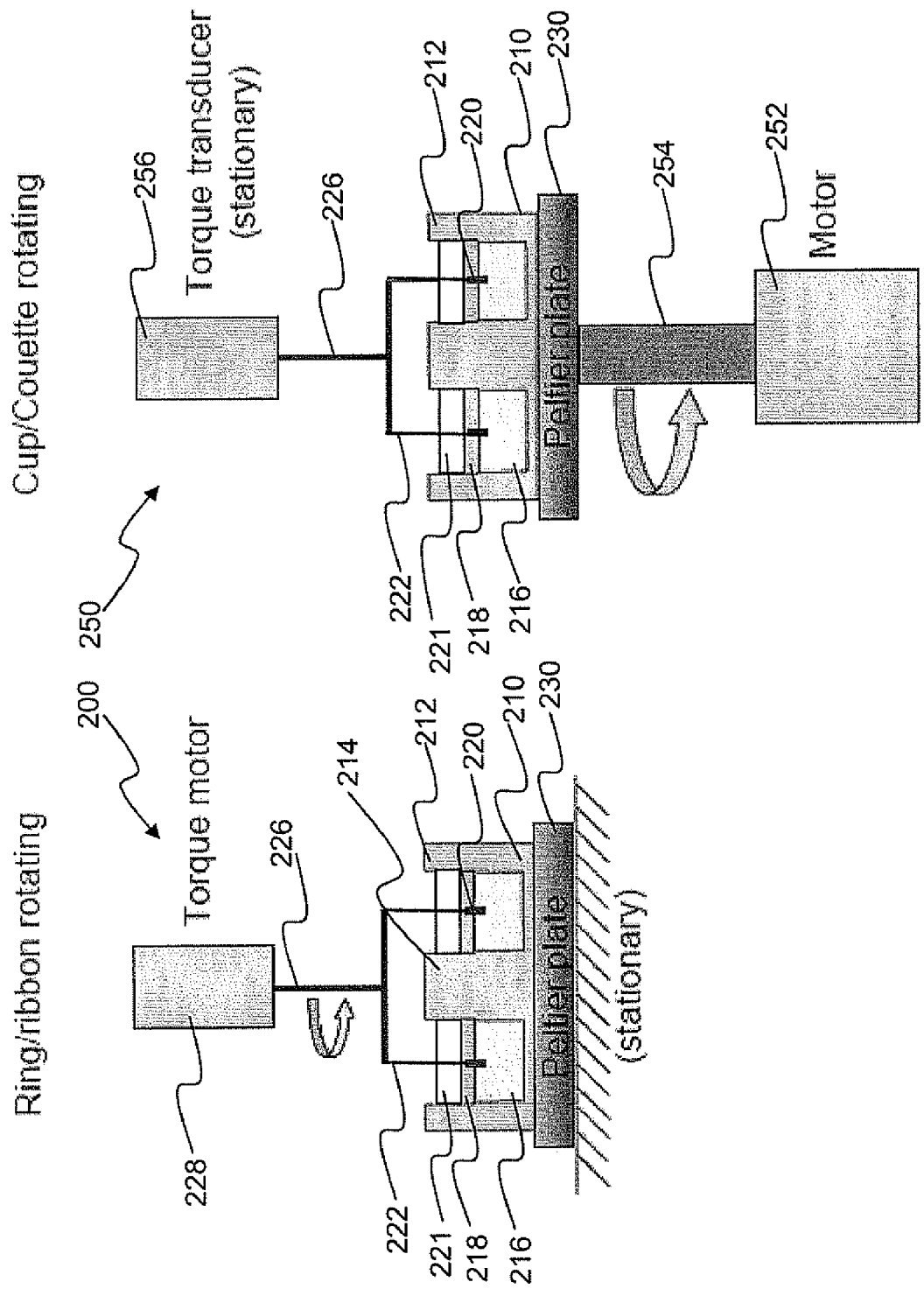
FIGS. 2a and 2b illustrate respective side cross-sectional views of alternative configurations of the present invention in which a fluid chamber is held stationary and rotated, respectively, during rheological measurements of a fluid interface.

FIGS. 2a and 2b illustrate alternative configurations of the present invention, in which a fluid chamber is held stationary (FIG. 2a) and rotated (FIG. 2b), respectively, during rheological measurements of a fluid interface. FIGS. 2a and 2b provide systems in which the rheological properties of fluid interfaces can more easily and more accurately be determined, as described below. In particular, the geometrical configurations described in the following paragraphs allow for more accurate correction of the sub-phase contribution to the interface shear properties measured using a rotational rheometer. Additionally, shear rate calculations can be simplified by selection of appropriate ribbon shape and chamber radii, as described below.

FIG. 2a depicts a side cross-sectional view of a rotating ribbon (stationary fluid chamber cylinder) rheometric system 200 comprising a cylindrical chamber 210. Chamber 210 includes chamber wall 212 and inner cylinder 214, which is arranged concentric with the cylindrical axis of chamber 210. Inner cylinder 214 can be, for example, a solid cylinder. Chamber 210 is configured to retain fluid in the region between chamber wall 212 and inner cylinder 214. Inner cylinder 214 and chamber wall 212 are mechanically coupled in this and other embodiments of the present invention described below, so that there is no relative rotational or translational motion between inner cylinder 214 and chamber wall 212. Rheometric measurements of fluid interfaces can be performed by providing a first fluid "sub-phase" in the bottom portion of chamber 210, such as sub-phase 216. Interface layer 218 (not drawn to scale for typical situations in which the layer may have microscopic thickness) is arranged on top of fluid sub-phase 216 at a level in which fluid interface 218 is intersected by ribbon 220. Ribbon 220 is also arranged such that it intersects the top region of sub-phase 216. When a rotation is applied to ribbon 220, the torque can be measured in order to probe the mechanical properties of interface layer 214.

Notably, as discussed above, interface layer 218 may constitute a thin region between an overlayer 221 and sub-phase 216. As discussed above, in some embodiments of the present invention, overlayer 221 can be another liquid phase. Alternatively, overlayer 221 may simply be the ambient gas phase above a liquid, such as air, in which case air layer 221 would not exhibit a top boundary as depicted in the Figures. In other words, interface layer 218 can be a layer having a thickness of a few monolayers or less that is disposed between a liquid sub-phase 216 and surrounding gas phase, such as air 221.

Figure 2C:
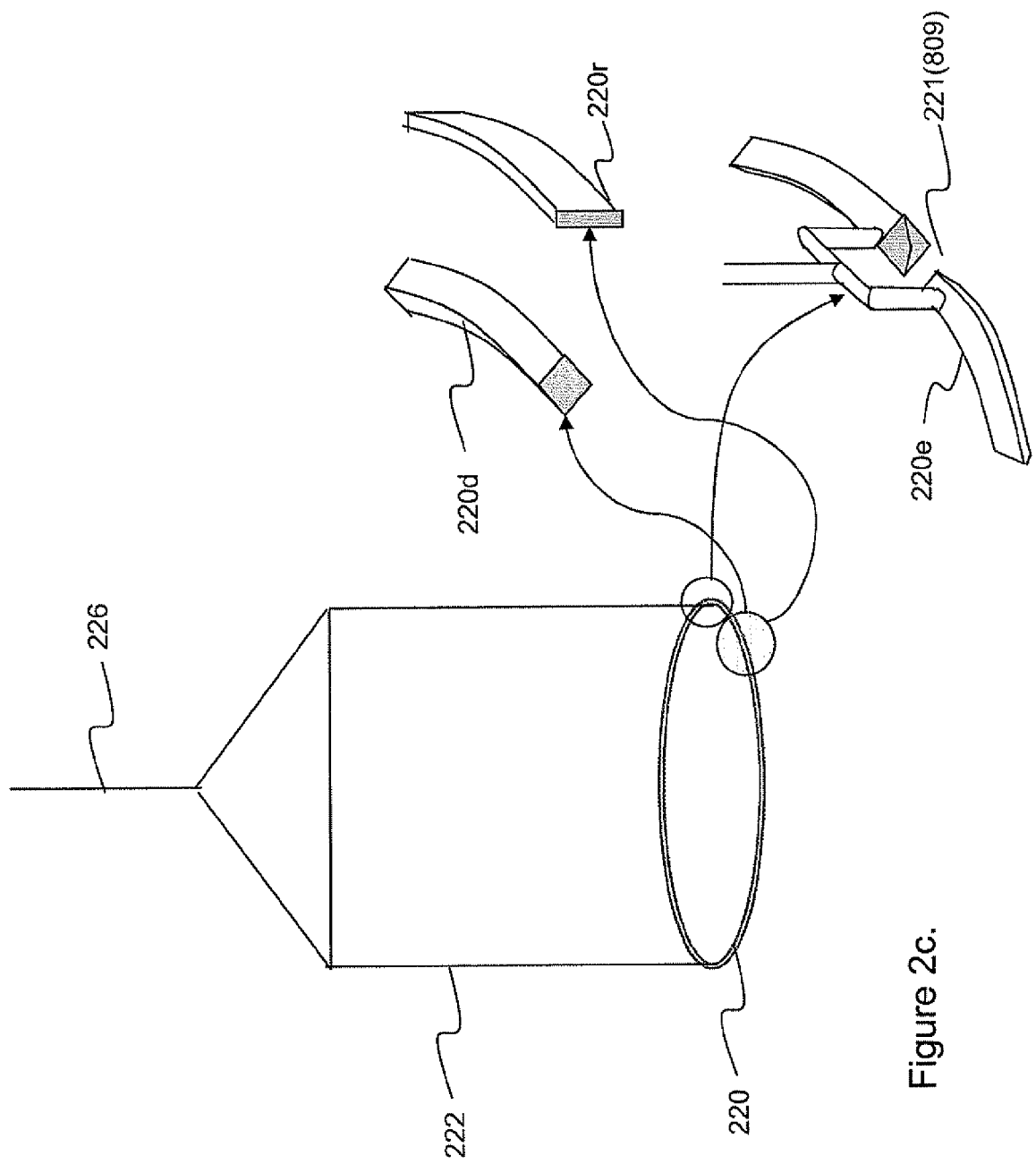
FIG. 2c depicts in perspective view alternative cross-sectional shapes of a ribbon suspended from two narrow wires or rods, in accordance with embodiments of the present invention.

FIG. 2c depicts in perspective view alternative shapes for a ribbon in a device arranged according to a preferred configuration of the invention applicable to systems illustrated in FIGS. 2a and 2b, in which two narrow suspension wires or rods 222, preferably separated by about one hundred eighty degrees, suspend ribbon 220 between chamber wall 210 and inner cylinder 214. In additional embodiments of the present invention, three or more suspension members 222 are provided to suspend ribbon 220. For example, three wires, preferably spaced equally apart, or four wires, preferably spaced equally apart, can be used to suspend ribbon 220. As depicted further in FIGS. 3-5, ribbon 220 is arranged as a rigid circular structure that is concentric with the axis of chamber 210 and according to different embodiments can have various geometrical cross sections, for example, rectangular or diamond shape (see respective elements 220r and 220d in FIG. 2c). In addition, ribbon 220 can include an opening 221, as discussed further below with respect to FIG. 8b. Preferably, ribbon 220 comprises diamond shape structure in cross section, as illustrated in FIG. 2c, designed so that interface ribbon 220 can couple to the interface layer 218 and sub-phase 216 when ribbon 220 contacts the fluids, as discussed further below with respect to FIGS. 7a-7b.

Preferably, the thickness of ribbon 220 in the horizontal direction is small compared to the rheometer dimensions. However, the ribbon thickness should be sufficient to maintain rigidity of the ribbon. For example, the ratio of horizontal thickness of the ribbon 220 to the gap (distance) between inner cylinder 214 and chamber wall 212 is preferably less than a few percent. Accordingly, the ribbon thickness can be neglected when making shear calculations.

When suspension 226, comprising a control rod or shaft, is driven by torque motor 228, ribbon 220 rotates or oscillates within a horizontal region parallel to the fluid interface between sub-phase 216 and interface layer 218. Torque motor 228 can be, for example, a combined motor and transducer (CMT) of known design, or any other motor design that provides a measurement of torque output. As described further below with respect to FIG. 3, the mechanical properties of a fluid interface 218 can be more easily measured as compared to conventional rotational rheometers because the motion of fluid within a region between ribbon 220 and chamber wall 210 and within a region between ribbon 220 and inner cylinder 214 can be more easily modeled, leading to simpler calculations of the viscoelastic properties of interface 218.

System 200 can also include optional Peltier plate 230 that can be a conventional Peltier plate designed to vary the fluid temperature within chamber 210. Accordingly, the mechanical properties of interface layers can be measured as a function of temperature.

Figure 4:
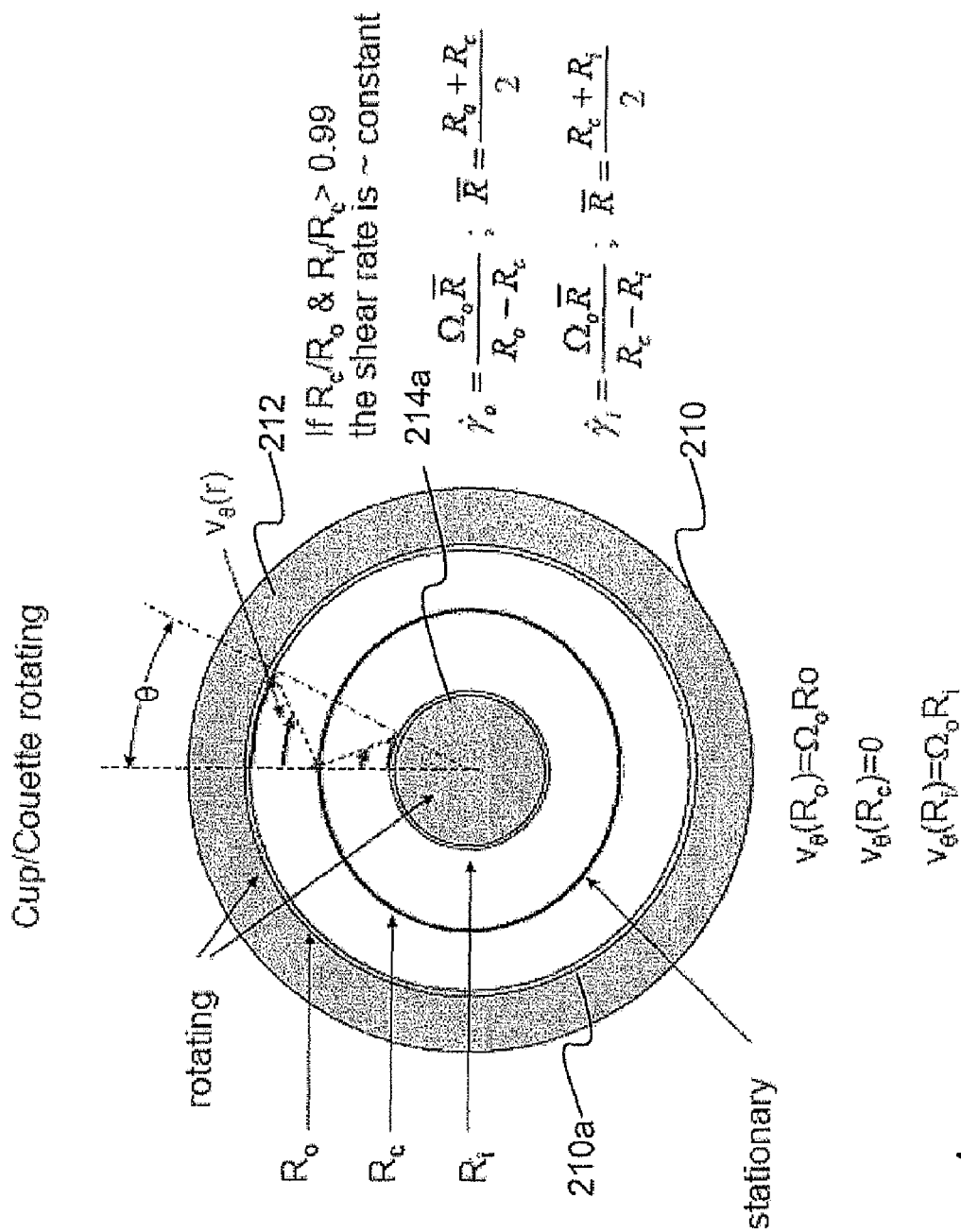
FIG. 4 illustrates a plan view of a rheometric device having a rotating chamber, according to an embodiment of the present invention.

FIG. 2b depicts an alternative configuration of the present invention, in which system 250 contains substantially the same elements as those depicted in system 200, except that a rotational drive is applied to the chamber 210, while no rotational movement is exerted upon ribbon 220 from suspension 226. Instead, suspension 226 is connected to a stationary torque transducer 256 that is configured to measure a torque sustained by ribbon 220 when chamber 210 is rotated by motor 252. As depicted in FIG. 2b and FIG. 4, both chamber wall 212 and inner cylinder 214 rotate when motor 252 applies a rotation to chamber 210. This causes a relative motion of fluid within chamber 210 that exerts a torque upon ribbon 220 that can be measured by transducer 256. The advantage of this type of configuration is that the torque measurement does not need to be corrected for motor inertia and friction as is the case when a CMT is used to drive the ribbon.

As with system 200, system 250 provides a configuration in which the fluid motion can be more readily modeled and calculated, leading to more accurate measurement of the mechanical properties of interface layer 218.

In a preferred embodiment of the present invention, the relative dimensions of ribbon 220, inner cylinder 214 and chamber wall 212 are arranged to simplify modeling and calculation of shear forces within chamber 210.

Figure 3:
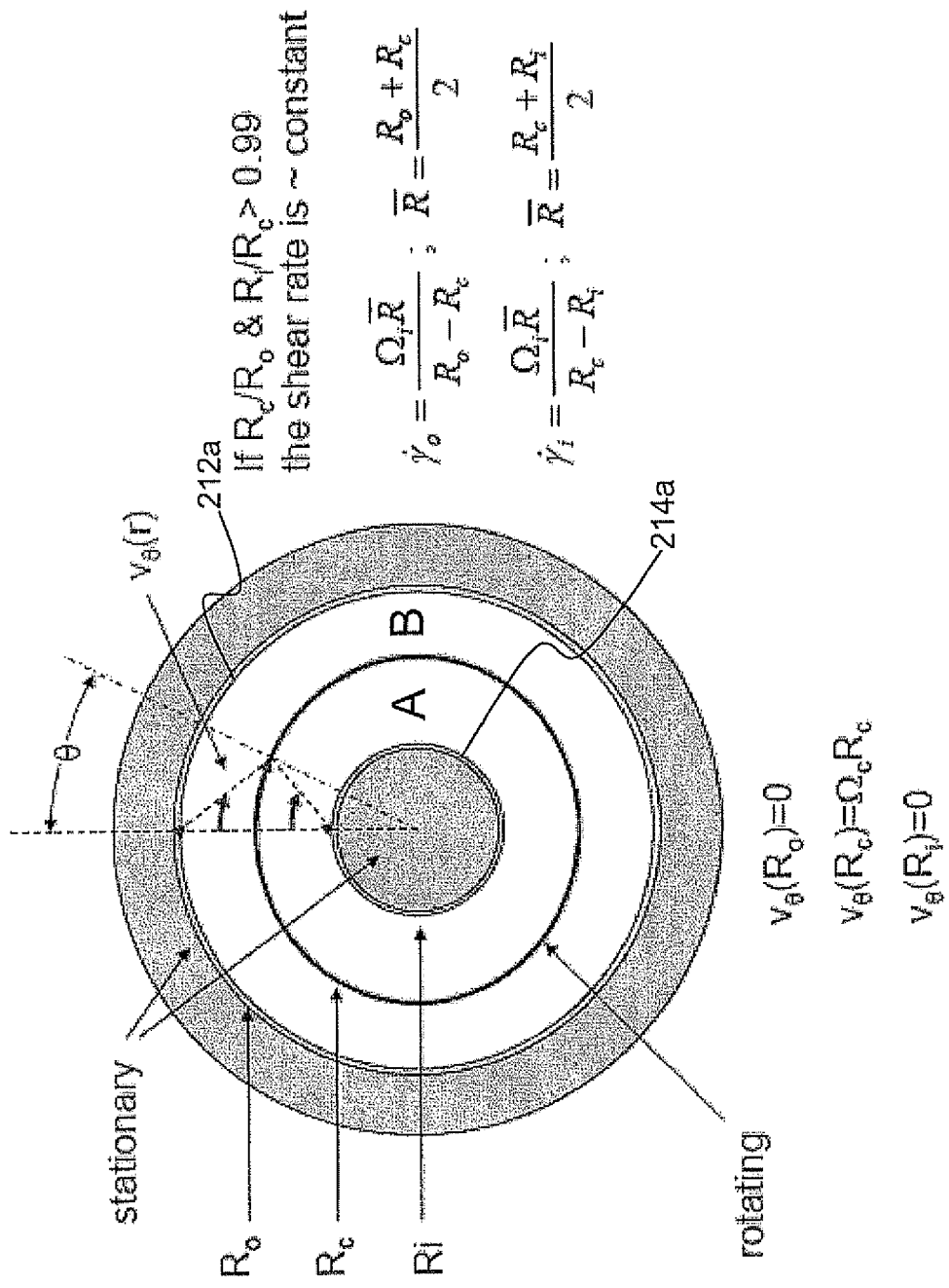
FIG. 3 illustrates a plan view of a rheometric device having a rotating ribbon, in accordance with an embodiment of the present invention.

FIGS. 3 and 4 depict plan views of aspects of two rheometer chambers arranged in accordance with alternative embodiments of the present invention. As discussed further below, in preferred embodiments of the present invention, the relative dimensions of ribbon 220, inner cylinder 214 and chamber wall 212 are the same for both chambers. The specific geometrical configurations depicted in FIGS. 3 and 4 are depicted as embodiments of respective systems 200 and 250 of respective FIGS. 2a and 2b.

FIG. 3 illustrates details of a rotating ribbon configuration of the present invention in which ribbon 220 is rotated by an external motor, such as motor 228 depicted in FIG. 2a. When ribbon 220 is suspended within a fluid and a rotation (or oscillation) is applied to ribbon 220, while chamber 200 (including wall 210 and inner cylinder 214) is held motionless, the fluid motion is as shown in inner region A between ribbon 220 and cylinder 214, as well as in outer region B between ribbon 220 and chamber wall 210. As noted, the fluid velocity $V_\theta$ as a function of the ribbon radius $R_c$ is equal to $\Omega_c R_c$, where $\Omega_c$ is the angular velocity of the ribbon.

In locations near the ribbon 220, the velocity is at a maximum approaching the angular velocity of the outer surface of ribbon 220. At the vertical wall surface 214a of cylinder 214 and at the inner vertical wall surface 212a of chamber wall 212, the fluid motion can be assumed to be zero. The interface fluid shear rate thus depends on the angular velocity of the ribbon and the dimensions of the chamber. By placing a rotating ribbon that is concentric with and located in between inner cylinder 214 and chamber wall 210, the shear properties of the region between ribbon 220 and cylinder 214 are more well defined, which allows any contribution from the sub-phase fluid to be evaluated and corrected for, leading to a more accurate characterization of the fluid interface mechanical properties.

In accordance with a preferred embodiment of the present invention, the radius $R_c$ of ribbon 220 is arranged in conjunction with the radius $R_i$ of inner cylinder 214 and radius $R_o$ of inner surface of chamber wall 210 in a manner so as to provide an average fluid shear rate $\gamma_i$ in region A ($\gamma_i = \Omega R/(R_c - R_i)$), that is approximately equal to an average fluid shear rate $\gamma_o$ in region B ($\gamma_o = \Omega R/(R_o - R_c)$). By selecting such radii dimensions, the modeling of shear in an interface layer 218 can be more accurately performed, leading to more accurate calculations of the mechanical properties of layer 218 measured by torque motor 228.

Preferably, as described further below with respect to FIG. 5, the relative radii are arranged to produce a same average shear in regions A and B according to the "narrow gap" model.

FIG. 4 depicts details of a Couette rotating cup configuration of the present invention in which ribbon 220 is held without external rotation from suspension 226, while a rotation is applied to wall 210 and inner cylinder 214, as depicted in FIG. 2b. When ribbon 220 is suspended within a fluid and a rotation (or oscillation) is applied to chamber 200 including wall 210 and inner cylinder 214, the fluid motion is as shown in inner region A between ribbon 220 and cylinder 214, as well as in outer region B between ribbon 220 and chamber wall 210. In locations near the ribbon 220, the velocity is assumed to be about zero in the fluid region approaching the outer surface of ribbon 220. Near wall 210a, the fluid velocity approaches the angular velocity of the rotating chamber wall $V_\theta(R_o)$, while near wall 214a, the fluid velocity approaches the angular velocity of the rotating wall $V_\theta(R_i)$.

In accordance with a preferred embodiment of the present invention, in the configuration of the invention shown in FIG. 4, the radius $R_c$ of ribbon 220 is also arranged in conjunction with the radius $R_i$ of inner cylinder 214 and radius $R_o$ of inner surface of chamber wall 210 in a manner so as to provide an average fluid shear rate in region A approximately equal to an average fluid shear rate in region B.

Figure 5:
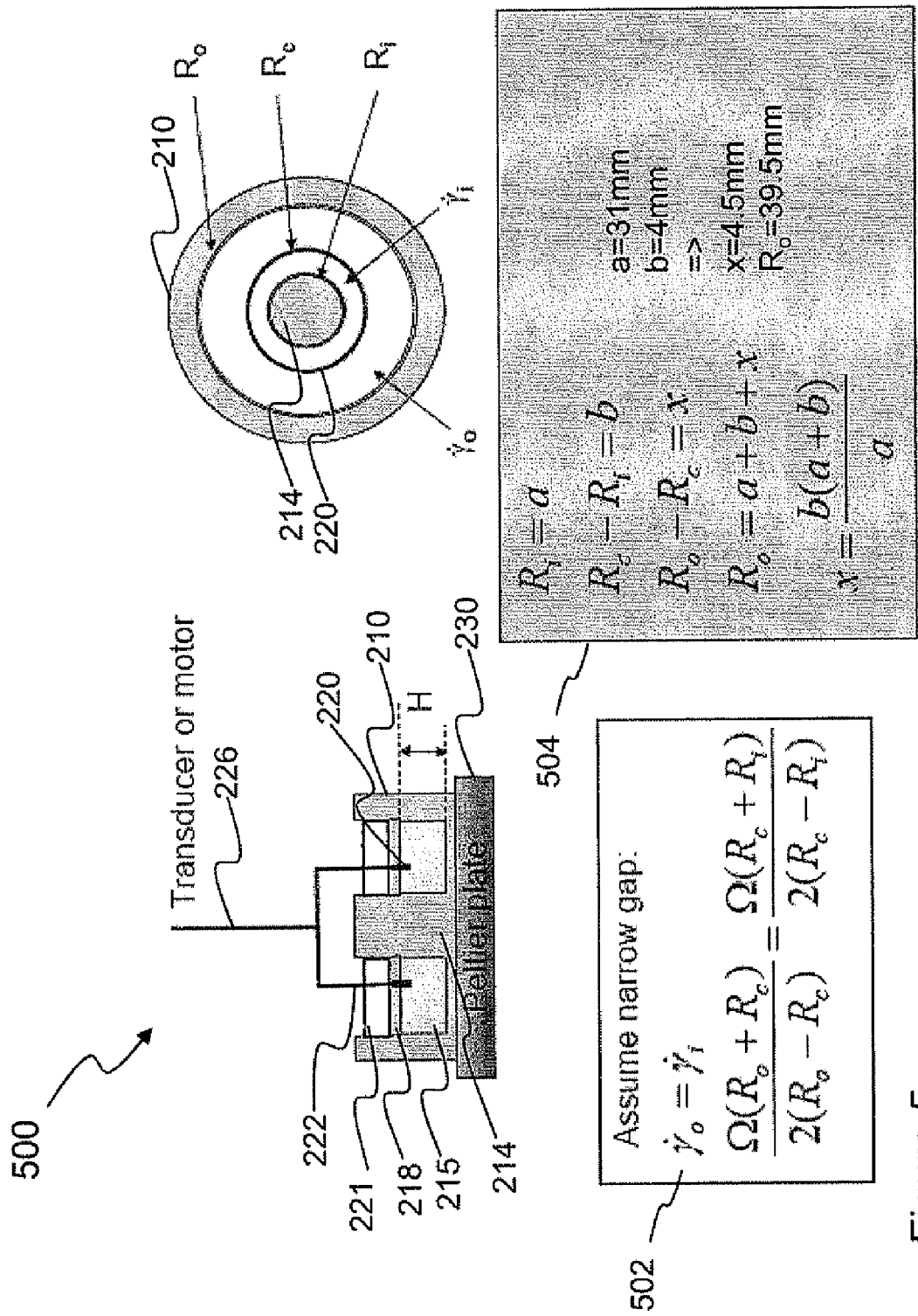
FIG. 5 shows details of geometrical parameters of a rheometric device depicted in side cross-sectional and plan views, in accordance with an embodiment of the present invention.

FIG. 5 depicts a recipe 502 that contains an exemplary set of dimensions for a rheometer system in accordance with a preferred embodiment of the present invention. The rheometer system 500, shown in cross-sectional and top down views, has those features common to systems 200 and 250 described above. Rheometer system 500 can be configured in either a rotating ribbon configuration described with respect to FIGS. 2a and 3, or a Couette configuration described above with respect to FIGS. 2b and 4.

In order to simplify calculation of shear properties of an interface fluid 218, the desired ribbon radius $R_c$ for a rheometer can be determined from the equations shown in the recipe box 502 in FIG. 5, which are based on a narrow gap model for the chamber and ribbon geometry. Under the narrow gap model, the average fluid shear rate in the inner region $\gamma_i(\Omega(R_o+R_i)/2(R_c-R_i))$ is assumed to be equal to the fluid shear rate $\gamma_o$ (or $\Omega(R_o+R_c)/2(R_o-R_c)$) in the outer region, which means that under the narrow gap model, equation 504, $(\Omega(R_o+R_c))/2(R_o-R_c)=\Omega(R_o+R_i))/2(R_c-R_i)$, can be used to set the relative dimensions of the radius of ribbon 222, the radius of inner cylinder 214 and that of the inside of chamber wall 210.

Thus, in order to produce this equivalency of inner and outer shear rate, the radius of ribbon 220 $R_c$ is arranged to be a quantity b larger than the radius $R_i$ (also termed "a") of inner cylinder 214, that is, $R_c-R_a=b$. The radius $R_o$ of outer wall surface 210a is arranged to be a quantity x larger than $R_o$ (Ro−Rc=x), where x=b(a+b)/a. In the example shown in recipe 502, $a=R_i=31$ mm, $b=R_c-R_a=4$ mm, leading to a value for x of 4.5 mm, and a value for $R_o$ of 39.5 mm and $R_c$ of 35 mm.

Thus, in one exemplary implementation of the present invention, the radius of inner cylinder 214 is 31 mm, the ribbon 220 radius $R_c$ is 35 mm, and the chamber wall inner surface 210a radius is 39.5 mm. Using a rheometric apparatus having respective components that have those radii, or radii proportionately scaled to have the same relative ratios (that is, any convenient set of radii that have the relative ratios of 31:35:39.5), the calculation of shear properties of an interface layer 218 is simplified because the average fluid shear rates in regions A and B can be assumed to be equal and curvature effects on shear distribution can be neglected.

In the narrow gap model in which the equations shown in FIG. 5 strictly apply, the ratio of $R_c/R_o$ and $R_i/R_c$ are assumed to be about 0.99 or greater. In other words, the ratio of $R_i/R_o$ ($R_c/R_o \times R_i/R_c$) is about 0.98 or greater, which implies that both regions A and B are narrow as compared to radius $R_i$. In accordance with embodiments of the present invention, a chamber can be constructed so that a ribbon having an $R_c$ intermediate between the $R_o$ and $R_i$ is disposed in a narrow gap in which the narrow gap model strictly applies. In the latter case, the equation 502 produces the result that $R_c$ is very nearly 0.5 $(R_o+R_i)$.

For practical reasons, however, it may be preferable to construct rheometers whose chambers have wider regions A and B so that a ribbon can be conveniently placed therein. Thus, in the example shown in FIG. 5 in recipe box 504, the relative dimensions of the respective radii do not strictly satisfy the narrow gap model. Nevertheless, in embodiments of the present invention, the narrow gap model is used to determine relative dimensions of a ribbon radius as compared to an inner cylinder and chamber wall radius. This produces a geometrical configuration in which average shear rates inside and outside of the ribbon can be assumed to be equal as a first approximation. As illustrated in the exemplary recipe 504, application of the narrow gap method for setting the relative results in the radius of the ribbon being closer to that of the inner cylinder ($R_c-R_i=4$ mm) than to that of the chamber wall ($R_o-R_c=4.5$ mm). In another example, in accordance with an embodiment of the present invention that applies the narrow gap model to arrange the relative chamber wall, inner cylinder and ribbon radii, if $R_i=15$ mm and $R_c=20$ mm, then $R_o=26.7$ mm.

It will be understood by those of skill the art that in systems having dimensions such as those shown in FIG. 5, taking into account curvature will produce a still more refined calculation of fluid shear rate in regions A and B, which is a complex function of the radius r in systems in which the narrow gap model does not strictly apply.

In order to accurately probe the viscoelastic properties of a surface layer, it will be appreciated that the actual surface geometry of fluids in the rheometric systems, such as those described above with respect to FIGS. 2a-5, should correspond to the dimensions defined by the apparatus. In other words, in addition to accurately defining the relative radii of inner cylinder wall 214a, chamber wall 210a, and ribbon 220, the subphase surface should be flat between the ribbon and inner cylinder and outer chamber walls. Referring again to FIG. 2a, it is important that the interface layer 218 wet ribbon 220 properly and extend to walls 210a and 214a so that the surface of interface layer 218 is substantially flat. In many liquid systems to be measured, the materials properties of the liquid, as well as the properties of the walls of the rheometer, cause the surface interface layer 218 to deviate significantly from a substantially flat surface. For example, due to the curvature introduced by a meniscus, the distance along a nominally horizontal surface of a sub-phase, such as water, is difficult to accurately measure. The meniscus can constitute a region up to several millimeters thick, which prevents the use of "narrow gap" geometries that may have horizontal gaps between the ribbon and chamber walls on the order of a millimeter. This inability to accurately measure the "horizontal" dimension of the interface region above the sub-phase meniscus prevents accurate calculation of the interface shear rate. Accordingly, by eliminating or reducing the meniscus, the geometry of regions A and B in the interface region is better defined, and provides for the ability to construct narrow-gap chambers in which the relative ratios of ribbon and chamber wall radii conform to the narrow gap model discussed above.

In accordance with embodiments of the present invention, a rheometric device, such as those depicted in FIGS. 2a and 2b, can be provided with one or more features that serve to reduce or suppress the meniscus on the top surface of a sub-phase, to pin the interface at the top surface of the sub-phase, or do both. The term "interface pinning" denotes the immobilization of a boundary (interface) of a liquid at a point where the liquid contacts the solid. The boundary of the liquid can be a boundary between two liquids or a liquid/gas phase boundary. Thus, a pinned interface region adheres to a specific location along a solid surface, such as a specific location of a chamber wall of a rheometer.

The shape of a meniscus on a liquid surface depends on a balance between surface forces that define how well the liquid wets the surface of the solid and gravitational forces acting on the fluid elements.

Figure 7A:
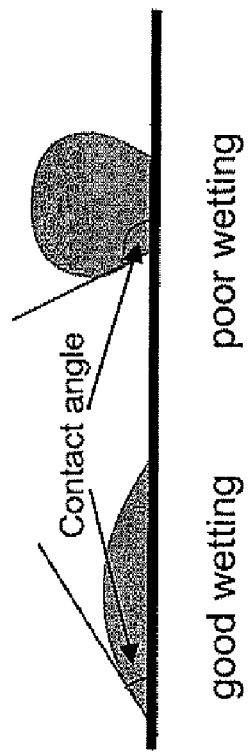
FIG. 7a illustrates variations in contact angle of a fluid on a surface as a function of wetting ability.

The process of wetting a surface is illustrated using two different wetting scenarios in FIG. 7a, for a liquid (fluid) on a horizontal surface. The surface curvature of the fluid-air interface at the boundary to a solid depends on the contact angle. For good wetting, the contact angle is small, while for poor wetting, the contact angle is large. Water, for example, has good wetting properties when in contact with platinum and iridium, but poor wetting properties when in contact with Teflon. Thus, a liquid contained in a container having vertical walls can form a meniscus whose cross-sectional shape ranges from concave to convex depending on its tendency to wet the container walls.

I addition to the tendency of a fluid to wet a solid surface and gravitational forces acting on the fluid, the shape of the solid surface of a container can also influence the meniscus formed at the top of a fluid. As discussed further below, in embodiments of the present invention where interface pinning features are supplied on a solid surface, the shape of a meniscus is influenced by the geometrical shape of the solid surface at the interface pinning point.

By immobilizing the liquid interface at the top of the liquid of interest is at a plurality of pinning points, such as at a specific height along a wall of the inner cylinder, a corresponding height along a chamber wall, as well as a set of surfaces provided on a rotating ribbon, and by suppressing meniscus formation, rheometric systems designed in accordance with embodiments of the present invention facilitate formation of a liquid interface that is flatter between the rheometric system walls and the ribbon. Thus, the relative radii $R_c$, $R_i$ and $R_o$ of the rheometric apparatus can be used to accurately define the actual length of the liquid surface of a liquid disposed between an inner cylinder and ribbon, as well as the length of the liquid surface between the ribbon and chamber wall.

FIGS. 6a-6f illustrate details of variants of a system 600 arranged in accordance with embodiments of the present invention. Referring now to FIG. 6a, system 600 contains elements common to systems 200 and 250 described above, such as ribbon 220 and suspension 226. In addition, chamber 602 includes an inner cylinder 610 having an interface-pinning feature 612. In one embodiment of the present invention, illustrated in FIG. 6b, the interface-pinning feature is a ledge 612a located on inner cylinder wall 614. Ledge 612a defines the boundary between a lower and upper cylindrical portion of cylinder 610a, in which the lower portion has a slightly greater radius. Preferably, a similar ledge region 622 is located in chamber wall 620 (not shown).

In addition to the embodiment depicted in FIG. 6b, as illustrated in FIG. 6c, the interface-pinning feature can be a rim 612b having a sharp triangular cross-section. The interface-pinning feature can also be a notch 612c provided around the circumference of and extending into inner cylinder 610c, such as a notch having a sharp triangular cross-section, as depicted in FIG. 6d.

In another embodiment of the present invention, the interface-pinning feature is a boundary between two materials having substantially different surface energies, where the boundary is located on at least one of the inner cylinder and the outer chamber wall. For example, as depicted in FIG. 6e, a band 612d is provided on inner cylinder 610d, where the band is a material of dissimilar surface energy to the rest of cylinder 610d. The band is preferably flush with the cylinder surface 614 and defines a boundary BD at which the surface energy of the cylinder wall 614 changes substantially, which facilitates suppression of a meniscus on the surface of a liquid phase whose level reaches the boundary BD. In accordance with an embodiment of the present invention, a band of dissimilar surface energy to the rest of the inner cylinder can comprise the entire top portion 612e of a cylinder 610e, in which case cylinder 610d comprises two cylinders having dissimilar surface energies and stacked on top of the other, as depicted in FIG. 6f.

In another embodiment of the present invention, a band of material having a first surface energy is provided as a thin coating on a cylinder having a second surface energy that is substantially different from the first surface energy. For example, band 612d can be a coating of Teflon® that is provided on a steel inner cylinder 610d. Alternatively, the whole upper portion 612e of an inner cylinder 610e can comprise a thin coating provided only on the top portion of cylinder 610e.

Figure 6H:
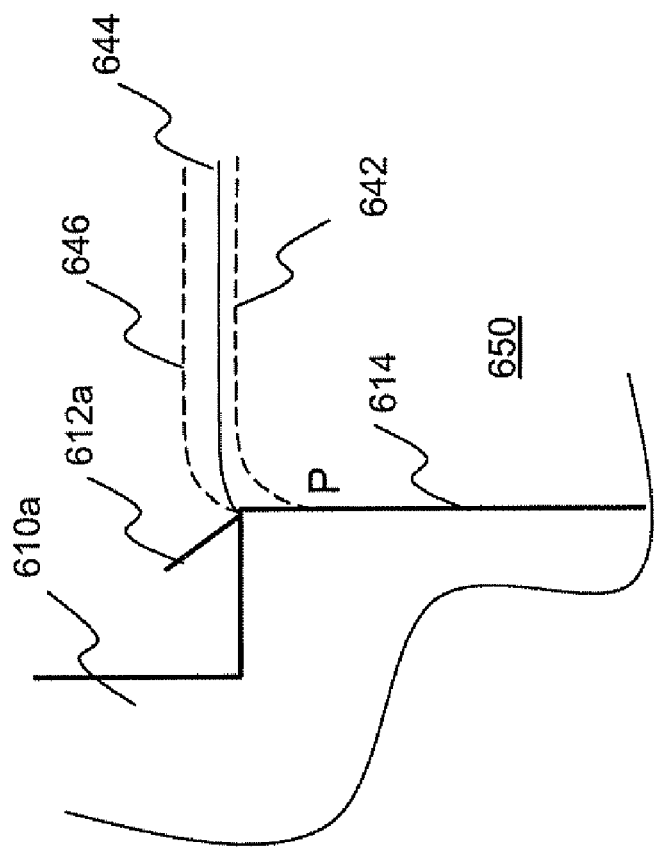
FIGS. 6g and 6h depict in perspective view details of the interaction of a liquid with a rheometer wall provided with a ledge-feature, in accordance with an embodiment of the present invention.
Figure 6G:
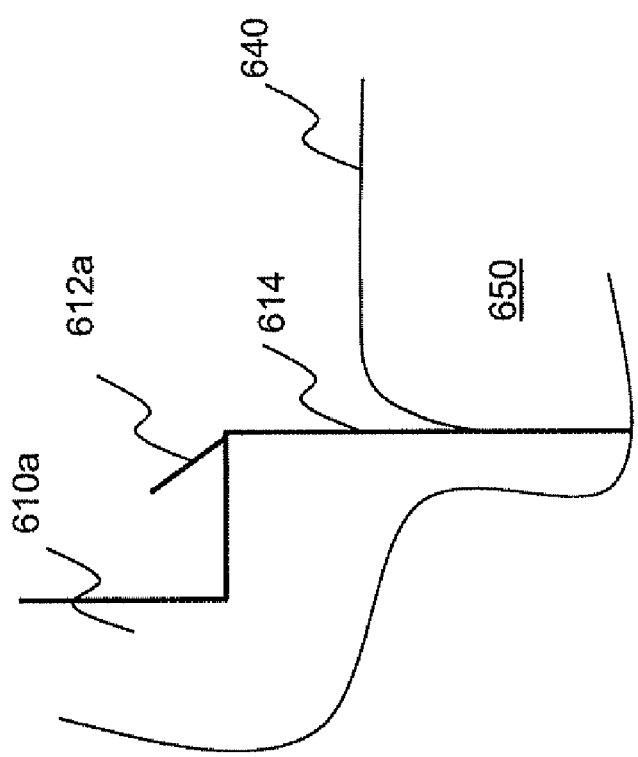

FIGS. 6g and 6h depict in perspective view details of the interaction of a liquid 650 with a rheometer wall provided with a ledge-feature in accordance with an embodiment of the present invention. For example, the ledge can represent feature 612a of inner cylinder 610a. However, in other embodiments, the ledge feature can be provided in a chamber wall of a rheometer device. In accordance with an embodiment of the present invention, the wall 614 comprises a material that tends to repel liquid 650, such that liquid 650 has poor wetting properties with respect to wall 614. For example, liquid 650 can be water, and wall 614 and ledge 612a can be Teflon®. As depicted in FIG. 6g, the contact angle is large and the surface 640 of liquid 650 is convex. FIG. 6h depicts scenarios in which liquid 650 is filled to a higher level near the level of ledge 612a. When the contact point P of liquid 650 is still below the level of ledge 612a, the surface 642 of liquid 650 retains a strong convex meniscus. When the liquid level is increased beyond point P, the contact point with wall 614 reaches the level of the ledge as depicted for surface 644. Due to the change of the orientation of the solid surface where wall 614 meets ledge 612a, the horizontal surface of ledge 612a influences the orientation of the contact angle formed between surface 644 and the solid surface. This causes the liquid surface to become more level and the meniscus is thereby reduced. At the same time, because the liquid 650 is repelled by the surface of wall 614 and 612a, the drive to minimize the contact between liquid 650 and the surfaces of cylinder 610a forces the liquid to be pinned at the corner of the ledge and not to cover the horizontal surface, that is, the liquid does not spread over ledge 612a. As a result, the interface is pinned to the solid surface at the corner of ledge 612a and the meniscus is reduced. It is to be noted that there is an optimum filling height for pinning surface 644 while at the same time reducing the meniscus. Adding more liquid, which causes the average level of the liquid to increase, causes an increase in the meniscus, as depicted for surface 646. As noted previously, if the level is not sufficiently high (surface 642), pinning does not take place and moving water will destabilize the pinning point.

In addition to the ledge feature depicted in FIG. 6b, the triangular rim feature of FIG. 6c, the triangular notch feature of FIG. 6d, and the boundary feature between wall regions of dissimilar surface energy depicted in FIGS. 6e and 6f all serve to pin a liquid interface and reduce its meniscus as the liquid is filled to the level of the feature of interest.

Referring again to FIGS. 6a and 6b, in a preferred embodiment of the present invention, in a first step a sub-phase fluid (liquid) is added to chamber 602 until the top surface of sub-phase fluid is at the level H of an interface-pinning feature, such as ledge 612. As noted above, the presence of ledge 612 can be used to reduce or substantially eliminate any meniscus effect that could result if the fluid contacted a cylindrical wall having no ledge. As sub-phase fluid is added to the chamber, an operator can observe the meniscus disappear (the term "disappear," as used herein, denotes that the feature appears to decrease in size, whether or not the feature becomes completely unobservable to a user) at the point where the liquid level reaches the ledge height. Preferably, at that point, no more sub-phase liquid is added. In a subsequent step, ribbon 220 is lowered into contact with the surface of the sub-phase liquid, after which the interface layer is placed on the sub-phase. Alternatively, the interface layer can be placed on the sub-phase before lowering of ribbon 220 to contact the sub-phase surface. Accordingly, the horizontal distances along the top surface of the sub-phase liquid (that is, along the interface layer) between the ribbon and inner cylinder and between the ribbon and outer cylinder are well defined, and are not subject to uncertainties due to the presence of a meniscus, which could create a large measurement uncertainty. This inventive method and system helps avoid measurement inaccuracies that be introduced using many common fluid systems.

As discussed above, in order to develop improved methods and apparatus for well defined shear measurements at a fluid interface, it is desirable for the gap between the ribbon and cylinder wall to be small in comparison to the ribbon radius. As the gap becomes small, therefore, the fluid interface should ideally show minimum boundary imperfections, which means that it is desirable that the flat (horizontal)

portion of the interface surface extend as close as possible not only to the walls of the rheometer chamber but also to the edge of the ribbon.

In this regard, it is to be noted that the use of a diamond cross-section of a ribbon in accordance with embodiments of the present invention also helps to promote a flat interface where the liquid sub-phase/interface layer intersect the ribbon, thereby improving the quality of the measurements. This can be better understood with reference to FIG. 7b, as discussed below.

In general, the geometrical shape of the ring also has an important influence on the curvature of the interface at the solid boundary where the fluid contacts the ring.

In the case of excellent wetting by a fluid of a ribbon material, the fluid tends to spread on a solid surface. In the case of ribbon cross-sections presenting a vertical solid surface with respect to the interface, the interfacial film creeps up the vertical solid boundary. A curvature of the film results from a balance of surface forces which promote the wetting and gravity.

Figure 7B:
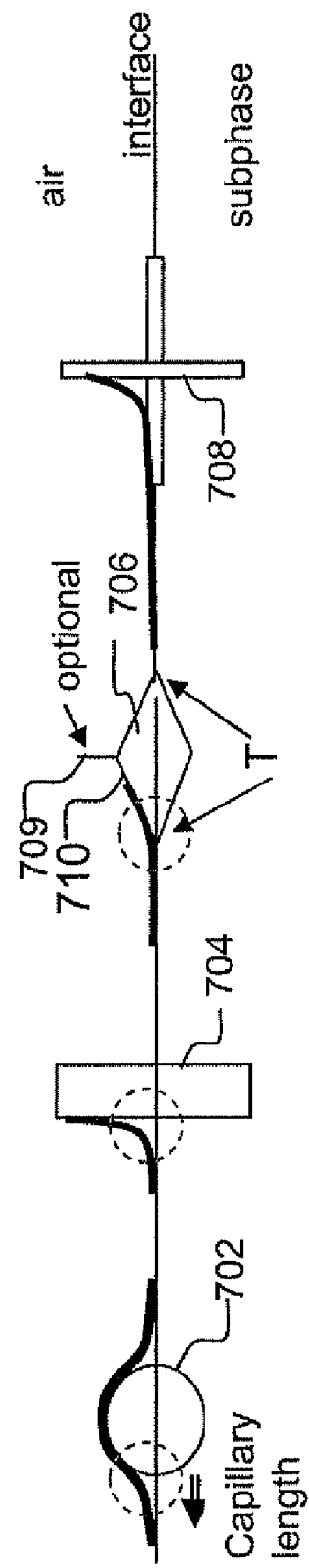
FIG. 7b illustrates details of wetting of ribbon surfaces for various ribbon cross-sectional shapes, in accordance with embodiments of the present invention.

As discussed below with respect to FIG. 7b, in choosing a ribbon cross-section, tradeoffs exist, for example, between producing a flatter interface (less film curvature) and ensuring that the interface is sheared by the ribbon. FIG. 7b illustrates alternative cross-sectional designs for ribbons used to measure interface layer properties using a rotating rheometer, in accordance with embodiments of the present invention. As illustrated for each different ribbon cross-sectional design, the interface is located in the middle of the cross-section of the ribbon. In FIG. 7b, the interface is depicted as located between a sub-phase, such as water, and air. The interface layer itself (not explicitly shown) may constitute a monolayer thick film. However, as discussed above, instead of air, a macroscopic layer comprising a second liquid could be located above the interface.

The ribbon material depicted in FIG. 7b is a material that is easily wet by the liquid.

The circular cross-section illustrated for ribbon 702 is not the best design for achieving a flat interface, since, at the interface, the solid ribbon surface has an angle of 90° (vertical) with respect to the interface. However, because of the curvature of the solid surface, the film may not rise too high out of the horizontal surface, and the capillary length is accordingly reduced in comparison to a ribbon 704, which has a rectangular cross-section. One particular advantage of this embodiment is that it is relatively easy to fabricate a circular ribbon having a circular cross-section. A disadvantage of the circular cross-section ribbon (or "ring"), depicted in FIG. 7b, is that the smooth curvature imparted by the circular cross-section may cause the film to spread completely over the ring and not couple with the ring at all. In other words, an interface layer may spread over the entire ribbon, such that the ribbon does not "cut" the interface layer. In this case, no shear deformation can be applied to the interface.

Of the designs shown in FIG. 7b, ribbon 704, which comprises a rectangular cross-section, presents a large obstacle to an interface film spreading completely over the ribbon. Thereby, coupling of (shearing of) the interface film to (by) the ribbon is guaranteed. However, the curvature near the ribbon is larger compared to the other designs illustrated, thereby reducing the extent to which the flat interface surface approaches the ribbon.

By providing a horizontal solid surface at the interface, ribbon 708, which has a "cross" cross-section, increases the extent to which the flat interface approaches the vertical portion of the ribbon, but curvature still exists.

The ribbon 706 having a diamond cross-sectional extends the flat portion of the interface to the solid ribbon. Due to the sharp edge and the non vertical solid surface, the curvature is reduced significantly, and as such, the capillary length is decreased. This arrangement provides the most accurate control of the distance along the interface between ring and wall. Since the diamond shape has a constant slope, rather than a smooth curvature, the possibility of the film on one side of the ring coupling with film on the other side is reduced as opposed to a circular shape. Optionally, the ribbon 706 could be outfitted with a vertical barrier 709 as shown, to ensure that the interface is sheared.

In embodiments of the present invention in which a water sub-phase is used in conjunction with a diamond-cross-section ribbon, the water tends to wet the upper diamond surface 710 when the water level reaches the level of the horizontal diamond tips for ribbons mad of material such as Pt and Ir that are easily wet by water. Nevertheless, the contact angle for water on such a metal surface is not zero, such that the wetting proceeds only to a point on surface 710 defined by the balance of surface forces and the gravitational force. Since the metal surface is obliquely inclined, the interface creeps up the surface 710 and couples well with the surface. Because of the oblique solid surface, the water film on the surface is very thin, such that the meniscus that builds up at the front end is small compared to a meniscus forming on a vertical surface. Because of this thin layer, the interface is in direct contact with the solid surface of the ribbon. Accordingly, using the diamond ribbon configuration, the interface region can be assumed to move at the same speed as the ribbon during a rheological test.

In accordance with an embodiment of the present invention, the ribbon radius used for the ribbon radius used for calculation of the interface shear deformation is the radius at the horizontal tips of the diamond shaped ring. Thus, the term $R_c - R_i$ becomes $R_{c1} - R_i$, and the term $R_o - R_c$ becomes $R_o - R_{c2}$, where $R_{c1}$ is the radius of the inner tip of the diamond cross-section ribbon (the horizontal tip of the diamond closest to the inner cylinder), and $R_{c2}$ is the radius of the outer tip of the diamond cross-section ribbon.

The inventors have determined that an embodiment of the present invention in which a diamond-cross-section ribbon is supported by three wires is capable of measuring interfacial shear viscosity one decade lower than that achieved by a double cone arrangement having the same diameter.

Other embodiments of the present invention include any geometrical shape that reduces the capillary length and enhances coupling of the fluid and the solid boundary.

Figure 8A:
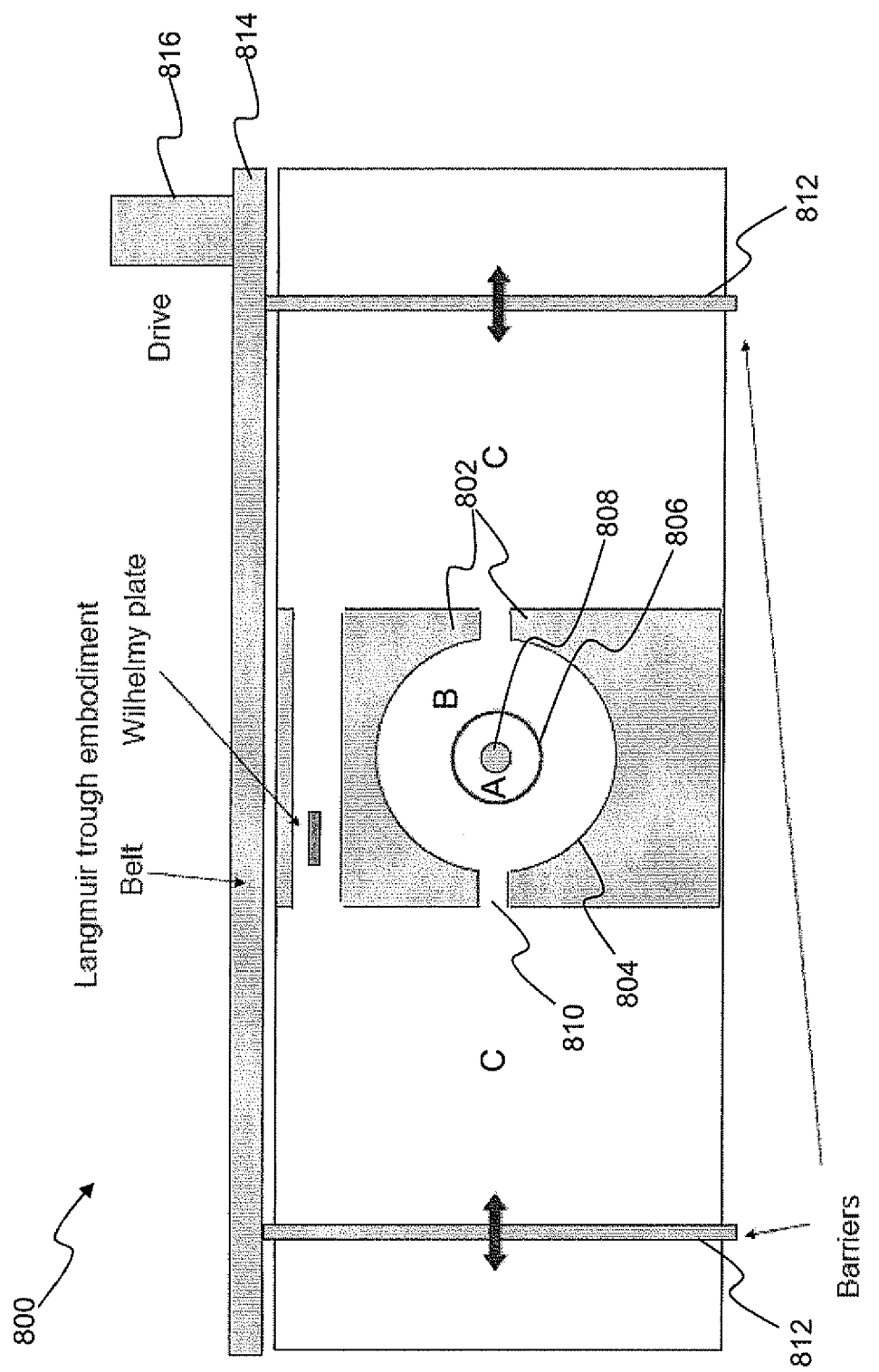
FIG. 8a illustrates a plan view of a rheometric device having a Langmuir trough, in accordance with another embodiment of the present invention.

FIG. 8a illustrates a top down view of a rheometric device 800 having a Langmuir trough, in accordance with another embodiment of the present invention. In this embodiment, body 801 comprises inner chamber wall portions 802 that define a cylindrical chamber 803 that has an inner surface 804 that corresponds to the chamber wall surface 210a illustrated in FIG. 2a. A ribbon 806 is suspended using a suspension (not shown) between the cylindrical inner surface 804 and inner cylinder 808. Ribbon 806 is configured to rotate or oscillate as described above with respect to FIG. 2a. Chamber wall portions 802 are separated by aperture regions 810, which preferably extends through the entire height of chamber block 801 and permits fluid to flow into regions A and B from regions C. Barriers 812, which may constitute a pair of opposed flat plates, are configured to move as shown using belt 814 connected to drive 816, so that a surface fluid can be compressed by moving the barriers 812 towards one another Alternatively, instead of using a pair of flat plates, a Langmuir trough could be arranged with substantially circular outer barriers that can be moved inwardly, similar to the general arrangement of a Langmuir trough described by Matsumoto et al. (*Thin Solid Films* 280 1,2 (1996) 238-243). Preferably, this measurement takes place by placing the ribbon at the interface region of the sub-phase and surface phase, rotating the ribbon and performing measurements, removing the ribbon from the liquid, moving the outer barriers closer together, placing the ribbon at the interface region, and so on. Accordingly, shear property measurements obtained using a rotating ribbon configuration as described above with respect to FIGS. 2*a* and 3 can be measured as a function of compression of an interface fluid in the horizontal plane.

Figure 8B:
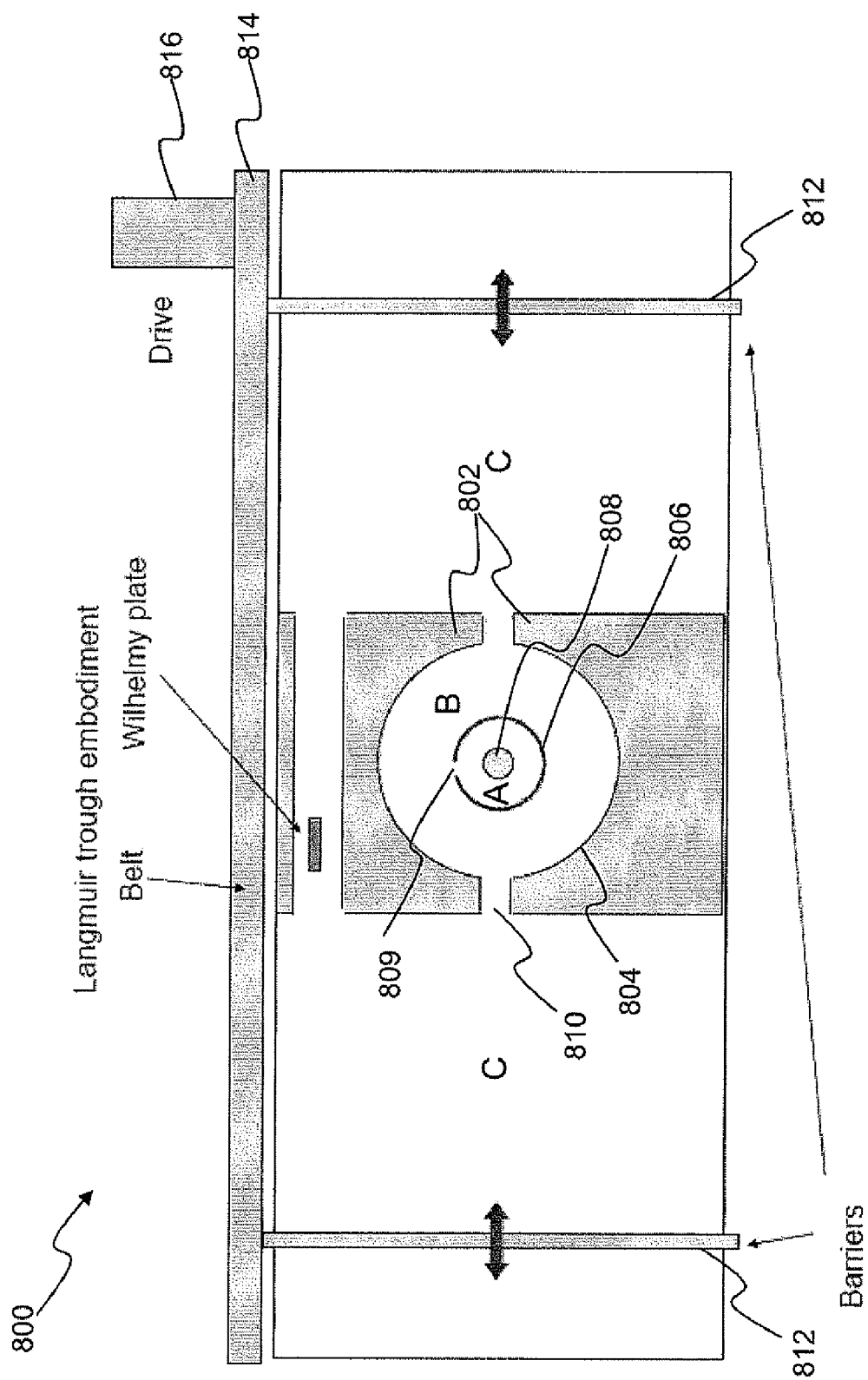
FIG. 8b illustrates a plan view of a variant of the rheometric device illustrated in FIG. 8a, in accordance with another embodiment of the present invention.

Alternatively, as depicted in FIG. 8*b*, in accordance with another embodiment of the present invention, an opening 809 can be provided in ribbon device 806 that breaks the ribbon. The opening is preferably located at the support points of the suspension as depicted in FIG. 2*c* for a diamond-shaped ribbon 220*e* having break 221. The ribbon opening permits the fluid surface to communicate between region B and A, while the ribbon is immersed in the fluid, which allows the fluid surface to be compressed without removing the ribbon from the liquid.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. Notably, the scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention

What is claimed is:

1. A measurement system for measuring rheological properties of a fluid interface, comprising:
a cylindrical chamber having a chamber wall whose inner surface defines an outer chamber radius with respect to an axis of the cylindrical chamber, the cylindrical chamber configured to retain a sub-phase that supports the fluid interface;
an inner cylinder disposed within the cylindrical chamber and concentric with an axis of the cylindrical chamber, the inner cylinder having an outer surface defining an inner cylinder radius, wherein the inner cylinder is mechanically coupled to the chamber wall to prevent relative rotational or translational movement between the inner cylinder and chamber wall;
a circular ribbon concentric with and suspended between the inner cylinder and chamber wall and configured to contact the interface,
wherein the circular ribbon has a ribbon radius ($R_c$) that is intermediate between the inner cylinder ($R_i$) and outer ($R_o$) chamber radii,
wherein the system is configured to impart a relative rotation to the circular ribbon with respect to the chamber wall and inner cylinder,
wherein the circular ribbon defines an inner region that lies between the circular ribbon and inner cylinder and an outer region that lies between the circular ribbon and chamber wall,
and wherein a ratio of the ribbon radius, inner chamber radius, and outer chamber radius is designed to yield an average shear rate in the inner region that is the same as an average shear rate in the outer region.

2. The system of claim 1, wherein the cylindrical chamber is coupled to a Peltier plate configured to vary the temperature of fluids contained in the cylindrical chamber.

3. The system of claim 1, wherein the circular ribbon comprises a cross section having one of a rectangular and diamond shape, the cross-section also having a horizontal dimension, wherein a ratio of the horizontal dimension to a gap equal to $R_o - R_i$ is less than a few percent.

4. The system of claim 1, further comprising:
a first interface pinning feature located on the inner cylinder, the first interface pinning feature defined by a boundary between a lower and upper cylindrical portion of the inner cylinder; and
a second interface pinning feature located on an inner surface of the chamber wall, the second interface pinning feature being at a same height as the first interface pinning feature and being defined by a boundary between a lower and upper cylindrical portion of the chamber wall.

5. The system of claim 1, wherein the circular ribbon is coupled to a torque motor configured to impart a rotation or oscillation of the circular ribbon about the axis of the cylindrical chamber and configured to measure a torque.

6. The system of claim 5, wherein the circular ribbon is coupled to two or more narrow vertical members arranged at equal angles apart, wherein the vertical members are coupled to a suspension that includes a central shaft that is suspended from the torque motor and configured to rotate around the axis of the cylindrical chamber in unison with the torque motor.

7. The system of claim 1, wherein the cylindrical chamber is coupled to a drive motor configured to rotate the chamber.

8. The system of claim 7, wherein the circular ribbon is mechanically coupled to a torque transducer configured to measure a torque imparted to the circular ribbon by fluid motion in the fluid interface.

9. The system of claim 8, wherein the circular ribbon is coupled to two or more narrow vertical members arranged at equal angle apart, wherein the vertical members are coupled to a suspension that includes a central shaft that is suspended from the torque transducer and configured to rotate around the axis of the cylindrical chamber.

10. The system of claim 1,
wherein $R_c = R_i + b$,
wherein $R_o = R_c + x$,
and wherein $x = b(R_c)/R_i$.

11. The system of claim 10,
wherein $R_c/R_o > 0.99$,
and wherein $R_i/R_c > 0.99$.

12. The measurement system of claim 1, further comprising:

a pair of apertures disposed on opposite sides between opposing portions of the outer chamber wall that are configured to allow fluid to flow into the cylindrical chamber;

a pair of opposed movable plates that define an external chamber communicatively coupled to the cylindrical chamber through the pair of apertures; and a drive motor configured to impart a relative translational motion to the movable plates, wherein the circular ribbon defines an inner region that lies between the circular ribbon and inner cylinder and an outer region that lies between the circular ribbon and outer chamber wall, and wherein a ratio of the ribbon radius, inner chamber radius, and outer chamber radius is designed to yield an average shear rate in the inner region that is the same as an average shear rate in the outer region, and wherein shear property measurements obtained using the rotating ribbon are measured as a function of compression of an interface fluid in the horizontal plane of the measurement system.

13. The system of claim 12, further comprising:

a first interface pinning feature located on the inner cylinder, the first interface pinning feature defined by a boundary between a lower and upper cylindrical portion of the inner cylinder; and a second interface pinning feature located on an inner surface of the chamber wall, the second interface pinning feature being at a same height as the first interface pinning feature and being defined by a boundary between a lower and upper cylindrical portion of the chamber wall.

14. A method of measuring mechanical properties of an interface, comprising:

filling a cylindrical measurement chamber with a liquid sub-phase until a meniscus of the liquid subphase is observed to disappear as a top surface of the sub-phase approaches a first height, wherein the cylindrical measurement chamber has an inner cylinder defined by a radius Ri that is concentric with an axis of the measurement chamber and an outer chamber wall defined by a radius Ro and concentric with the measurement chamber axis and mechanically rigidly coupled to the inner cylinder;

lowering a circular ribbon onto the top surface of the sub-phase, the circular ribbon having a radius $R_c$ that is intermediate between $R_i$ and $R_o$;

introducing an interface layer onto the top surface of the sub-phase; and introducing a relative rotational motion between the circular ribbon and the cylindrical measurement chamber when the circular ribbon is in contact with the interface layer and the sub-phase.

15. The method of claim 14, wherein the cylindrical chamber comprises:

a first interface pinning feature located on a surface region of the inner cylinder at the first height, the first interface pinning feature defined by a boundary between a lower and upper cylindrical portion of the inner cylinder; and a second interface pinning feature located on an inner surface of the outer chamber wall, the second interface pinning feature being at the first height and being defined by a boundary between a lower and upper cylindrical portion of the chamber wall, wherein the first and second ledges are configured to cause a meniscus on the top surface of the sub-phase to disappear as the top surface of the sub-phase reaches the first height.

16. The method of claim 14,
wherein Rc=Ri+b,
wherein Ro=Rc+x,
and wherein x=b(Rc)/Ri.

17. The method of claim 14,
wherein Rc/Ro>0.99,
and wherein Ri/Rc>0.99.

18. The method of claim 14, further comprising:

providing a plurality of apertures in the outer chamber wall that communicatively couple fluid in the cylindrical chamber with an external chamber region that surrounds the cylindrical chamber;

removing the ribbon from the liquid interface;

moving outer barriers at opposite ends of the external chamber region closer together so as to decrease an area of the top surface;

lowering the ribbon onto the top surface of the sub-phase; and introducing a relative rotational motion between the circular ribbon and the cylindrical measurement chamber when the circular ribbon is in contact with the interface layer and the sub-phase having the reduced surface area.

19. The method of claim 14, farther comprising:

providing a plurality of apertures in the outer chamber wall that communicatively couple fluid in the cylindrical chamber with an external chamber region that surrounds the cylindrical chamber;

providing an opening in the ribbon that allows communication between portions of the interface disposed outside the ribbon and portions of the interface disposed inside the ribbon;

moving outer barriers at opposite ends of the external chamber region closer together so as to decrease an area of the top surface; and introducing a relative rotational motion between the circular ribbon and the cylindrical measurement chamber when the circular ribbon is in contact with the interface layer and the sub-phase having the reduced surface area.

20. A measurement system for measuring rheological properties of a fluid interface, comprising:

a substantially cylindrical chamber having an outer chamber wall whose inner surface defines an outer chamber radius with respect to an axis of the cylindrical chamber;

an inner cylinder disposed within the substantially cylindrical chamber and concentric with an axis of the substantially cylindrical chamber, the inner cylinder having an outer surface defining an inner chamber radius, wherein the inner cylinder is mechanically coupled to the outer chamber wall to prevent relative rotational or translational movement between the inner cylinder and chamber wall;

a circular ribbon concentric with and suspended between the inner cylinder and outer chamber wall and configured to contact the fluid interface, wherein the circular ribbon has a ribbon radius ($R_c$) that is intermediate between the inner cylinder ($R_i$) and outer chamber ($R_o$) radii, wherein the circular ribbon includes an opening that allows communication between portions of the fluid interface disposed outside the circular ribbon and portions of the fluid interface disposed inside the circular ribbon;

a torque motor coupled to the circular ribbon through a suspension that is configured to impart to the circular ribbon a rotation that is concentric with the cylindrical chamber axis;

a movable plate means that defines walls of an external chamber surrounding the cylindrical chamber;

an aperture means to allow fluid to flow into the cylindrical chamber from the external chamber;

a drive motor configured to impart a relative translational motion to the walls of the movable plate means, wherein the circular ribbon defines an inner region that lies between the circular ribbon and inner cylinder and an outer region that lies between the circular ribbon and outer chamber wall, and wherein a ratio of the ribbon radius, inner chamber radius, and outer chamber radius is designed to yield an average shear rate in the inner region that is the same as an average shear rate in the outer region, and wherein the measurement system is configured to produce shear property measurements as a function of compression of an interface fluid in the horizontal plane of the measurement system.

21. The system of claim 20,
wherein $R_c = R_i + b$,
wherein $R_o = R_c + x$,
wherein $x = b(R_c)/R_i$,
wherein $R_c/R_0 > 0.99$,
and wherein $R_i/R_c > 0.99$.

22. The system of claim 20, further comprising:
a first interface pinning feature located on the inner cylinder, the first interface pinning feature defined by a boundary between a lower and upper cylindrical portion of the inner cylinder; and
a second interface pinning feature located on an inner surface of the chamber wall, the second interface pinning feature being at a same height as the first interface pinning feature and being defined by a boundary between a lower and upper cylindrical portion of the chamber wall.

23. A measurement system for measuring rheological properties of a fluid interface, comprising:
a cylindrical chamber having a chamber wall whose inner surface defines an outer chamber radius with respect to an axis of the cylindrical chamber, the cylindrical chamber configured to retain a sub-phase that supports the fluid interface;
an inner cylinder disposed within the cylindrical chamber and concentric with an axis of the cylindrical chamber, the inner cylinder having an outer surface defining an inner cylinder radius, wherein the inner cylinder is mechanically coupled to the chamber wall to prevent relative rotational or translational movement between the inner cylinder and chamber wall;
a first interface pinning feature located on the inner cylinder, the first interface pinning feature defined by a boundary between a lower and upper cylindrical portion of the inner cylinder; and
a second interface pinning feature located on an inner surface of the chamber wall, the second interface pinning feature being at a same height as the first interface pinning feature and being defined by a boundary between a lower and upper cylindrical portion of the chamber wall;
a circular ribbon concentric with and suspended between the inner cylinder and chamber wall and configured to contact the interface,
wherein the circular ribbon has a ribbon radius ($R_c$) that is intermediate between the inner cylinder ($R_i$) and outer ($R_o$) chamber radii, wherein the system is configured to impart a relative rotation to the circular ribbon with respect to the chamber wall and inner cylinder.

24. The system of claim 23,
wherein the circular ribbon defines an inner region that lies between the circular ribbon and inner cylinder and an outer region that lies between the circular ribbon and chamber wall,
and wherein a ratio of the ribbon radius, inner chamber radius, and outer chamber radius is designed to yield an average shear rate in the inner region that is the same as an average shear rate in the outer region.
wherein $R_c = R_i + b$,
wherein $R_0 = R_c + x$,
and wherein $x = b(R_c)/R_i$.

25. The system of claim 23,
wherein the first and the second interface pinning feature are one of:
a first and a second ledge provided on the inner cylinder and chamber wall, respectively;
a first and second triangular cross-section rim provided on the inner cylinder and chamber wall, respectively;
a first and second triangular cross-section notch provided in the inner cylinder and chamber wall, respectively;
a first and second boundary located on the inner cylinder and chamber wall respectively, the first and the second boundary each comprising a boundary between a lower surface having a first surface energy and an upper surface having a second surface energy that is substantially different from the first surface energy.

26. The system of claim 25,
wherein the first and the second interface pinning feature are a first and a second ledge provided on the inner cylinder and chamber wall, respectively,
wherein, on the inner cylinder, a lower cylindrical portion has a slightly greater radius than an upper cylindrical portion, and
wherein, on the chamber wall, a lower cylindrical portion has a slightly smaller radius than an upper cylindrical portion.

27. The system of claim 25, wherein the inner cylinder and chamber wall each comprise a material whose respective surface has a surface energy that is substantially different from that of the sub-base, wherein a contact angle of the sub-phase with the respective surface of the inner cylinder and chamber wall is high.

* * * * *